United States Patent
Geistert et al.

(10) Patent No.: US 8,660,661 B2
(45) Date of Patent: Feb. 25, 2014

(54) IMPLANTABLE ELECTRODE

(75) Inventors: Wolfgang Geistert, Rheinfelden (DE); Marc Kuttler, Berlin (DE)

(73) Assignee: Biotronik CRM Patent AG, Baar (CH)

(*) Notice: Subject to any disclaimer, the term of this patent is extended or adjusted under 35 U.S.C. 154(b) by 2282 days.

(21) Appl. No.: 11/185,144

(22) Filed: Jul. 20, 2005

(65) Prior Publication Data

US 2006/0020315 A1    Jan. 26, 2006

(30) Foreign Application Priority Data

Jul. 20, 2004    (DE) .......................... 10 2004 035 904

(51) Int. Cl.
*A61N 1/05*    (2006.01)
(52) U.S. Cl.
CPC ........................................ *A61N 1/05* (2013.01)
USPC .......................................................... 607/116
(58) Field of Classification Search
USPC ................................................. 607/119, 116
See application file for complete search history.

(56) References Cited

U.S. PATENT DOCUMENTS

| | | | |
|---|---|---|---|
| 3,842,843 A * | 10/1974 | Mourot et al. | 607/35 |
| 4,314,554 A | 2/1982 | Greatbatch | |
| 5,034,186 A | 7/1991 | Shimamune et al. | |
| 6,287,332 B1 | 9/2001 | Bolz et al. | |
| 6,304,786 B1 * | 10/2001 | Heil et al. | 607/126 |
| 2002/0035388 A1 | 3/2002 | Lindemans et al. | |
| 2002/0045926 A1 * | 4/2002 | Heil et al. | 607/116 |
| 2004/0098108 A1 * | 5/2004 | Harder et al. | 623/1.15 |

FOREIGN PATENT DOCUMENTS

| | | |
|---|---|---|
| DE | 30 20 200 A1 | 2/1981 |
| DE | 36 36 607 A1 | 5/1987 |
| DE | 103 28 816 A1 | 1/2005 |

OTHER PUBLICATIONS

English Translation of Office Action in corresponding Chinese Patent Application No. 200510087503.8 issued on Mar. 26, 2010.

* cited by examiner

*Primary Examiner* — Eric D. Bertram
(74) *Attorney, Agent, or Firm* — Arc IP Law, PC; Joseph J. Mayo

(57) ABSTRACT

The invention concerns an implantable electrode which includes at least one electrical conductor having a proximal connecting region for a pulse generator and at least one working electrode which can be connected to the pulse generator by way of the conductor. The implantable electrode includes at least one portion which contains elementary magnesium.

18 Claims, 3 Drawing Sheets

IMPLANTABLE ELECTRODE

BACKGROUND OF THE INVENTION

The invention concerns an implantable electrode which includes at least one electrical conductor having a proximal connecting region for a pulse generator and at least one working electrode which can be connected to the pulse generator by way of the conductor.

Electrodes of the general kind set forth are well-known from the state of the art. They are a component part of numerous functional electrostimulation devices (FES) which are used for the electrical treatment of nerve or muscle cells in the diagnostic or therapeutic sector. Implant systems for functional electrostimulation, include for example, cardiac pacemakers with a pulse generator for artificially stimulating cardiac actions, which is disposed in a body-compatible housing with associated electronic circuit and power supply. The housing has a connecting location to which the electrode is connected.

The term 'electrode' in medical technology denotes not only the transfer location for electrical energy in accordance with the physical definition but also relates to the line comprising the electrical conductor together with encasing insulation and all further functional elements which are fixedly joined to the line. Hereinafter, for purposes of clarity, the portion of the electrode which actually acts in the physical sense and which includes the transfer location for the electrical energy is referred to as the 'working electrode'.

The materials which are suitable for the purposes of such use should enjoy adequate bioresistance and also good biocompatibility. Accordingly it is necessary to ensure that long-term implantation in the body—that is to say in a highly corrosive environment—occurs without noteworthy breakdown processes and does not result in an unwanted immunological reaction. Biocompatible plastic materials based on silicone, polycarbonates, epoxysilanes, polyurethane, polysulfones, polyethylene and polyester present themselves as suitable for insulation of the electrical line. The working electrodes in turn which can be designed in the form of discharge, stimulation and measuring electrodes are generally formed on the basis of biocompatible metals such as platinum, iridium, titanium or gold.

Materials for use in implants are acceptable when the surrounding tissue reacts to mechanical disturbing influences and the presence of the material only to a slight extent with non-specific inflammation phenomena, even with an increased risk of allergy.

It has been found that tissue regions which are exposed to mechanical disturbing influences have a tendency to involve an increased immunological reaction or inflammation reaction. Electrodes have such regions inter alia at the connecting locations to the housing of the pulse generator as it is there that the geometries of the components impose limits on 'mechanically flexible deflection' of the electrode. A further area involving a particular loading is in the region of the working electrodes which in fact, to perform their function, must bear directly against the tissue to be stimulated. Here too unwanted immunological and inflammation reactions on the part of the body repeatedly occur. In addition electrodes frequently have to be provided with anchor elements or holding structures in order to ensure a relative spatial position of the working electrode with respect to the tissue to be treated. Immunological and inflammation reactions generally occur to an increased extent also in the regions of the holding structures and anchor elements which can be of many different configurations.

SUMMARY OF THE INVENTION

Accordingly an aspect of the present invention is to further improve the compatibility of implanted electrodes which include at least one electrical conductor having a proximal connecting region for a pulse generator and at least one working electrode which can be connected to the pulse generator by way of the conductor.

According to the invention that is achieved in that the electrode has at least one portion which contains elementary magnesium. It has surprisingly been found that elementary magnesium evidently exerts a positive influence on the surrounding tissue and counteracts strong immunological and inflammation reactions on the part of the body to the presence of the electrode. The operative mechanism which forms the basis for the effect has hitherto not been discovered. The desired effect occurs only when the magnesium is at least for a short time in elementary form—either as a pure element or as an alloy.

Preferably, the magnesium is in the form of a biodegradable magnesium alloy which contains at least 50% by weight, preferably at least 70% by weight and particularly preferably at least 85% by weight of magnesium. The term 'biodegradation' is used to denote hydrolytic, enzymatic and other metabolism-governed breakdown processes in the living organism, which lead to a gradual dissolution of at least large parts of the alloy. The term biocorrosion is frequently used synonymously. The term bioresorption additionally includes subsequent resorption of the breakdown products.

The alloy is preferably of type WE, that is to say it contains yttrium and rare earths as alloy components. The above-mentioned alloys can be well processed and in in-vitro tests have exhibited an antiproliferative effect on smooth muscle cells in a human being. They are thus particularly well suited to precluding unwanted reactions on the part of the body to the presence of the electrode. The processes involved in decomposition of the alloy possibly support or boost the antiproliferative effect.

Biodegradable magnesium alloys which contain rare earth metals and yttrium are particularly preferred, in which respect the collective term 'rare earth metal' stands for the elements scandium (atomic number 21), lanthanum (57) and the 14 elements following lanthanum, cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71) which are referred to as lanthanides. Particularly preferably, the magnesium alloys involve the following proportions by weight of the alloy components:

rare earth metals between 2.0 and 5.0% by weight and/or
yttrium between 3.5 and 4.5% by weight and/or
neodymium between 1.5 and 3.0% by weight and/or
zirconium between 0.3 and 1.0% by weight and/or
aluminum <0.5% by weight, in particular <0.01% by weight and/or
balance <0.5% by weight, in particular 0.3% by weight, wherein magnesium occupies the proportion by weight that remains to 100% by weight in the alloy. The above-mentioned magnesium alloys exhibit a favourable decomposition behaviour, high biocompatibility of the alloy and also the breakdown products and they have adequate mechanical properties for the area of use.

In accordance with a preferred variant of the above-indicated embodiment, the specific composition of the magnesium alloy and its modification are predetermined such that decomposition starts immediately after implantation and is maintained until the electrode is covered with connective tissue at least region-wise. That period of time should preferably be between 1 and 90 days, in particular between 3 and 30 days. The extent of the breakdown processes is dependent on the conditions prevailing at the implantation location. At least region-wise covering signifies that at least the regions of the magnesium-bearing portions are covered to more than 50% of their area with connective tissue.

In a strongly flowing tissue environment, a higher liberation rate for magnesium and/or its breakdown products must be predetermined to ensure the desired effect while, in a tissue environment with slight or no flow at all, a lower liberation rate in respect of the stated components is required to achieve the desired effect. The liberation rate is also dependent on the geometry of the portions and the magnesium content of the magnesium-bearing portions. Accordingly, in practice the magnesium-bearing portions of the electrode are to be adapted individually to the respectively desired application to achieve the desired liberation characteristic. It is known that a higher magnesium content leads to an increase in the decomposition speed. It is also known that processing the material, for example by extruding it, leads to a change in the metallic structure and in that way it is also possible to influence decomposition.

The portion can entirely or in parts comprise magnesium or its alloys. Preferably magnesium or its alloys is provided in the form of small metal particles which are embedded into a biodegradable matrix. With decomposition of the matrix, the particles are liberated and are also slowly broken down. The particles are preferably of a diameter of between 0.1 μm and 500 μm, in particular between 1 μm and 50 μm. Hyaluronic acid together with its derivatives is preferred as the matrix as that biopolymer is very quickly broken down and has an extremely high level of biocompatibility.

A magnesium-bearing 'portion' in accordance with the invention can assume any geometries. For example the line of the electrode, that is to say the electrical conductor with encasing insulation material, can be coated with magnesium or its alloys, over its entire extent. It is also possible for the portion to be integrated in the form of an independent structural element into the electrode, for example in the form of a ring of the material, which is drawn on to the line at a predetermined location. In that respect, particularly suitable configurations are those in which the magnesium-bearing portions are arranged at the proximal end of the electrode, that is to say adjacent to the connecting region for the pulse generator. Other preferred arrangements are those in which the portions are arranged beside the working electrodes. Finally, in accordance with a further preferred configuration, a magnesium-bearing portion is arranged on or beside the anchor elements or holding structures of the electrode. Experience has shown that tissue irritation effects occur to an increased degree in the tissues which, after implantation, bear against the stated regions of the electrode. The preferred configurations of the portions, which have just been described, again entirely or in parts, consist of magnesium or its alloys.

It is also advantageous if the magnesium-bearing portion covers an electrically active surface of the working electrode. After implantation and taking up its desired functionality, that region of the working electrode is particularly susceptible to immunological and inflammation reactions, which in part lead to scarring of the tissue and can thus have a sustained detrimental effect on the functionality of the working electrode. It has surprisingly been found that the presence of elementary magnesium does not substantially restrict the functionality of discharge electrodes, stimulation electrodes and measuring electrodes and in that respect exerts a positive suppressive effect on the immunological response of the surrounding tissue. The magnesium-bearing portion is preferably only a few micrometers, in particular 10-100 μm thick. The portion is further preferably designed in such a way that it has more than 90% by weight decomposed within between 1 hour and 120 hours, in particular between 12 hours and 36 hours. The above-described preferred configurations of the portions again entirely or in parts consist of magnesium or its alloys.

The active surface of the electrode preferably has cavities (recesses, slots, holes) which are filled with magnesium (alloy). In addition the entire active surface can also be provided with a thin coating of magnesium. That coating dissolves quickly and in the first few days causes alleviation of the acute reactions. The magnesium in the cavities then acts with a lower dose level over a longer period of time (some weeks).

BRIEF DESCRIPTION OF THE SEVERAL VIEWS OF THE DRAWINGS

The invention is described in greater detail hereinafter by means of embodiments by way of example and with reference to the accompanying drawings in which.

DETAILED DESCRIPTION OF THE INVENTION

Figure 1:
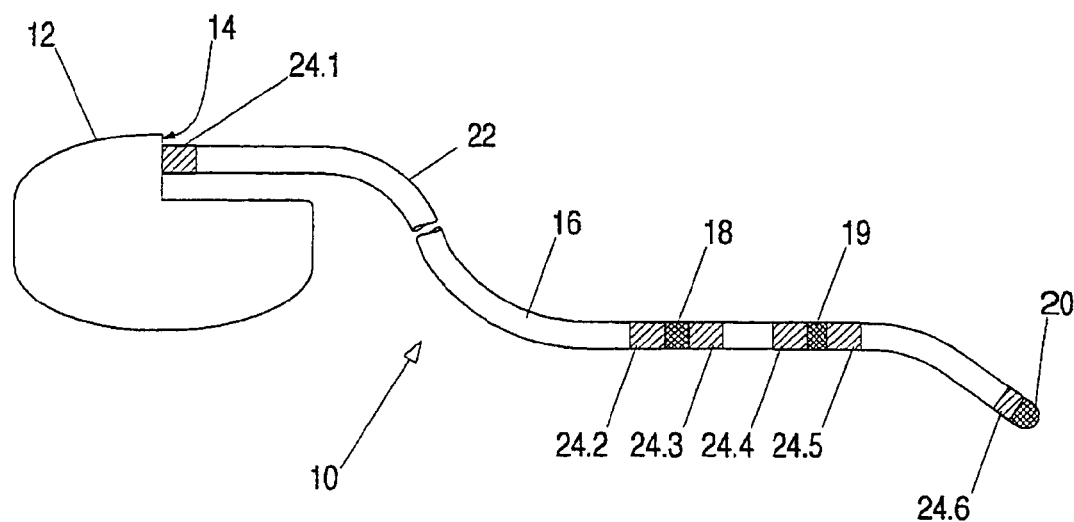
FIG. 1 shows an electrostimulation device in the form of a pacemaker with an electrode according to the invention.

FIG. 1 shows a diagrammatic view of a functional electrostimulation device 10 which is adapted for the electrical treatment of nerve or muscle cells, in particular for the artificial stimulation of cardiac actions. The electrostimulation device 10 can be divided into a housing 12 and an electrode 16 connected to the housing 12 at a connecting location 14. The housing 12 includes components necessary for the functionality of the electrostimulation device 10, such as a pulse generator, electrical circuits and a power supply.

At its proximal end, that is to say which is connected to the housing 12, the electrode 16 has suitable structures (not shown in greater detail here) which permit connection to the housing 12. Structures of that kind are sufficiently known from the state of the art and are of no further significance in connection with the present application so that they will not be described in detail here.

The electrode 16 has three working electrodes 18, 19, 20, that being used to denote electrically conductive structural elements which include a transfer location for the electrical energy. The two working electrodes 18, 19 are for example in the form of ring electrodes and can comprise a platinum-iridium alloy while the distal working electrode 20 forms a hemispherical head on the electrode 16 and comprises an iridium-coated platinum-iridium alloy. The working electrodes 18, 19, 20 can be in the form of discharge, stimulation or measuring electrodes. It is to be noted that the material, number, position and geometry of the working electrodes 18, 19, 20 can be varied within wide limits without that having significant effects on the subject-matter of the present invention.

The electrode 16 further includes a line 22 in which—not visibly illustrated here—one or more electrical conductors extend, the conductors being encased by an insulating material, in particular plastic material-based. The insulating material should enjoy at least tolerable biocompatibility and adequate bioresistance. Materials suitable for that purpose are sufficiently known to the man skilled in the art addressed in this respect.

The electrode 16 further has six magnesium-bearing portions 24.1 through 24.6. A first portion 24.1 is arranged adjacent to the connecting location 14 of the housing 12, that is to say in the region of the proximal end of the electrode 16. The magnesium-bearing portions 24.2 through 24.5 border the annular working electrodes 18 and 19. Finally the portion 24.6 directly adjoins the working electrode 20 at the distal end of the electrode 16. Experience has shown that it is possible to determine on the electrode regions which, after implantation, are the starting point to an increased degree for tissue irritation in the surrounding tissue. The portions 24.1 through 24.6 now extend in particular over those regions or are arranged at least adjacent thereto. That is based on the realisation that portions 24.1 through 24.6 which contain elementary magnesium can lead to a significant reduction in the irritation effects in the surrounding tissue. It will be appreciated that the entire line 22 can also be coated with a covering containing elementary magnesium, or a structural element of another kind.

The magnesium-bearing portions 24.1 through 24.6 can be implemented as follows:

1. The electrode 16 is masked with an aqueous 40% hyaluronic acid solution to which magnesium particles are added, sprayed and then dried. The process is repeated a plurality of times until a layer of a thickness in the region of between 0.1 and 1 mm is formed. The particles are preferably of a diameter of between 0.1 µm and 500 µm, in particular between 1 µm and 50 µm, and comprise a biodegradable magnesium alloy of type WE, specifically WE43, that is to say the alloy contains about 4% yttrium and about 3% rare earths, in particular neodymium. The commercially available material WE43 is extruded, atomised into fine particles by conventional processes and sieved. A proportion by weight of the magnesium particles, after the addition to the 40% aqueous hyaluronic acid solution, is about 1-5%.

In accordance with that first variant, accordingly magnesium particles are embedded in a biodegradable matrix and applied in the form of a coating to the electrode 16. Adhesion of the coating can possibly be improved by preliminary treatment of the target surfaces. That can include for example a plasma treatment or the application of a bonding agent layer.

2. In accordance with a second variant, the magnesium-bearing portions 24.1 through 24.6 can be integrated as independent metallic structural elements into the electrode 16. In the specific situation the magnesium-bearing portions 24.1 through 24.6 shown in FIG. 1 are drawn in the form of sleeves on to the line 22 and clamped fast or the sleeves sit in corresponding recesses in the line 22. The sleeves are of a wall thickness of between about 0.1 and 1 mm. The sleeve comprises magnesium or a biodegradable magnesium alloy, in particular of type WE.

Figure 2:
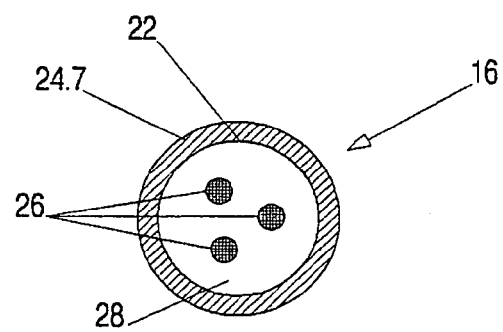
FIG. 2 shows a view in section through the electrode in the region of a magnesium-bearing portion.

FIG. 2 is a highly diagrammatic view in cross-section through the line 22 of the electrode 16 in the region of a magnesium-bearing portion 24.7. The electric line 22 includes a total of three electrical conductors 26 which are encased by an insulating material 28. Disposed in outwardly adjoining relationship is the magnesium-bearing portion 24.7 which is either in the form of a coating comprising a biodegradable matrix mixed with small magnesium particles or is of a solid nature in the form of a sleeve comprising a biodegradable magnesium alloy.

Figure 3:
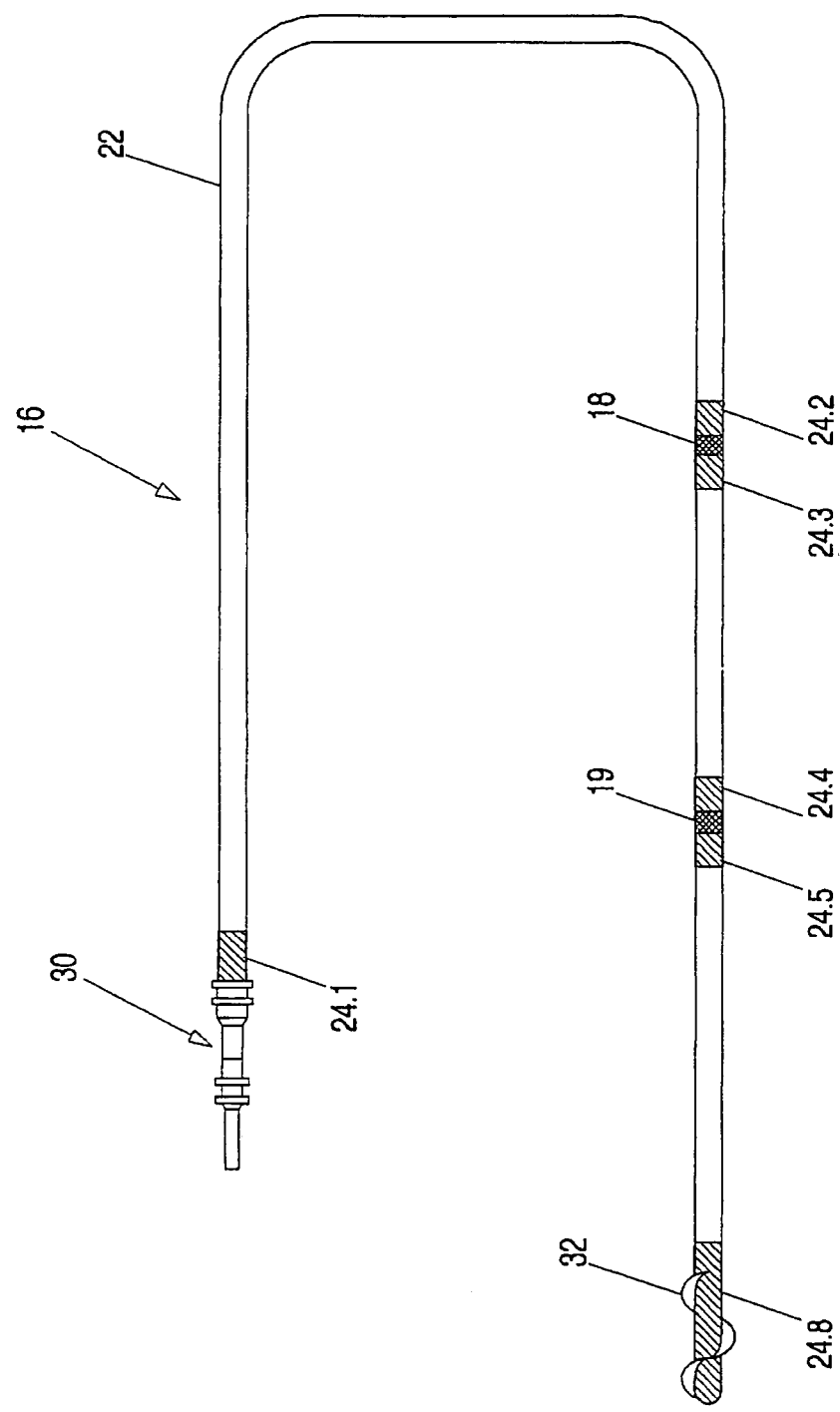
FIG. 3 shows a further variant of an electrode with an anchor element.

FIG. 3 shows a further electrode 16, in which respect components of the electrodes 16, which are of the same nature in functional terms, are denoted by the same references as in FIG. 1. The proximal connecting region 30 of the electrode 16 again carries a magnesium-bearing portion 24.1. The two working electrodes 18, 19 are also delimited by magnesium-bearing portions 24.2 through 24.5. At its distal end the electrode 16 carries an anchor element 32 which extends in a helical configuration to the tip of the electrode 16 and is intended to provide for anchorage in the surrounding tissue after or upon implantation. The entire distal region of the electrode 16, in which the anchor element 32 is arranged, is covered by a magnesium-bearing portion 24.8. The portion 24.8 can be implemented in the form of a coating comprising a biodegradable matrix with added magnesium particles. In that respect attention is directed to the variant 1 of the procedure described in relation to FIG. 1.

Figure 4:
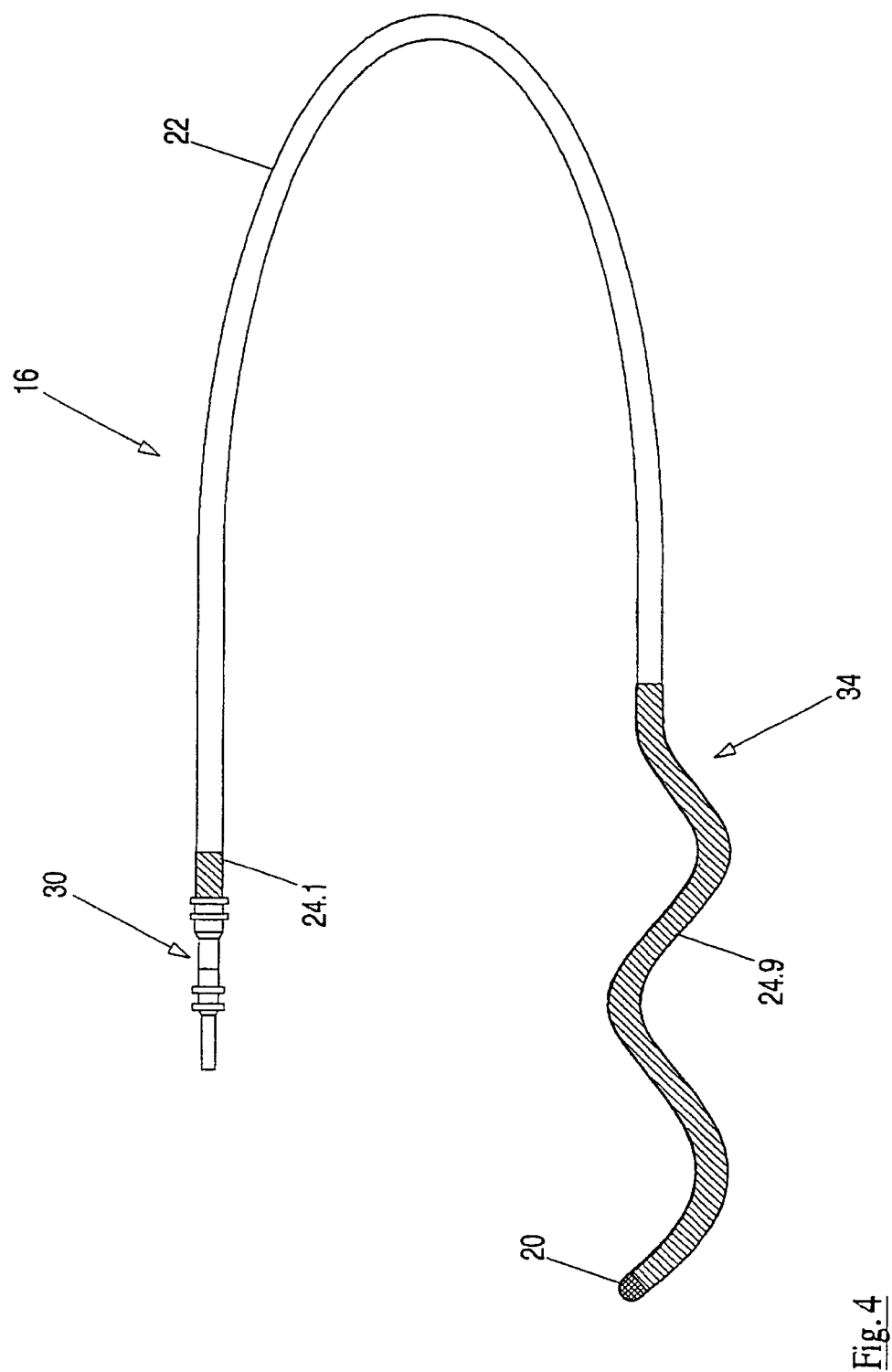
FIG. 4 shows a further variant of an electrode with a holding structure.

FIG. 4 shows a further alternative embodiment of the electrode 16 in which a holding structure 34 is intended to hold the electrode 16 in the desired position after implantation. The holding structure 34 is in the form of a coil-shaped portion of the electrode 16 and is intended to be able to bear against the surrounding tissue, by virtue of its configuration. The entire distal region of the electrode 16, which adjoins the working electrode 20, and thus also the holding structure 34, are completely covered by a magnesium-bearing portion 24.9. The portion 24.9 can again be covered in the form of a coating, as can be illustrated for example in the variant 1 in FIG. 1.

What is claimed is:
1. An implantable electrode which comprises
at least one electrical conductor having
a proximal connecting region for a pulse generator, and
a distal region; and
at least one working electrode configured to be connected to the pulse generator by way of the at least one electrical conductor,
wherein the at least one working electrode comprises an electrically active surface;
wherein the implantable electrode includes
at least one portion which contains
elementary magnesium in a form of metal particles,
wherein the metal particles are of a diameter between 0.1 µm and 500 µm;
wherein the elementary magnesium is configured such that a first period of time of decomposition starts immediately after implantation and is maintained until at least region-wise the implantable electrode is covered with connective tissue, such that the at least region-wise comprise at least regions of the elementary magnesium-containing portion that are covered to more than 50% of area with said connective tissue;
wherein the first period of time is between 1 and 90 days; and
wherein the elementary magnesium-containing portion is immediately adjacent to the at least one working electrode; and,
at least one magnesium-bearing portion;
wherein the at least one magnesium-bearing portion covers the electrically active surface of the at least one working electrode;
wherein the at least one magnesium-bearing portion comprises a thickness between 10-100 µm and is configured such that a second period of time of decomposition is maintained, and such that the at least one magnesium-bearing portion comprises more than 90% by weight decomposed; and wherein said second period of time is between 1 hour and 120 hours.

2. The implantable electrode as set forth in claim 1, wherein the elementary magnesium is in a form of a biodegradable alloy.

3. The implantable electrode as set forth claim 2, wherein at least a first magnesium-bearing portion of the at least one magnesium-bearing portion is arranged at said proximal connecting region of the implantable electrode.

4. The implantable electrode as set forth in claim 2, wherein the at least one working electrode comprises a plurality of working electrodes, such that a first working electrode and a second working electrode of said plurality of working electrodes are in the form of ring electrodes, and a third working electrode of said plurality of working electrodes is arranged at said distal region, and wherein said at least one magnesium-bearing portion comprises a plurality of magnesium bearing portions, such that at least a first magnesium-bearing portion of said plurality of magnesium bearing portions is carried on said proximal connecting region, at least a second magnesium-bearing portion of said plurality of magnesium bearing portions entirely covers said distal region and directly adjoins said third working electrode, and at least a third magnesium-bearing portion of said plurality of magnesium bearing portions borders said first working ring electrode and said second working ring electrode.

5. The implantable electrode as set forth in claim 2, wherein the biodegradable alloy is an alloy of type WE.

6. The implantable electrode as set forth claim 5, wherein at least a first magnesium-bearing portion of the at least one magnesium bearing portion is arranged at said proximal connecting region of the implantable electrode.

7. The implantable electrode as set forth in claim 5, wherein the at least one working electrode comprises a plurality of working electrodes, such that a first working electrode and a second working electrode of said plurality of working electrodes are in the form of ring electrodes, and a third working electrode of said plurality of working electrodes is arranged at said distal region, and wherein said at least one magnesium-bearing portion comprises a plurality of magnesium bearing portions, such that at least a first magnesium-bearing portion of said plurality of magnesium bearing portions is carried on said proximal connecting region, at least a second magnesium-bearing portion of said plurality of magnesium bearing portions entirely covers said distal region and directly adjoins said third working electrode, and at least a third magnesium-bearing portion of said plurality of magnesium bearing portions borders said first working ring electrode and said second working ring electrode.

8. The implantable electrode as set forth claim 1, wherein at least a first magnesium-bearing portion of the at least one magnesium-bearing portion is arranged said proximal connecting region of the implantable electrode.

9. The implantable electrode as set forth in claim 1, wherein the at least one working electrode comprises a plurality of working electrodes, and wherein at least a first magnesium-bearing portion of the at least one magnesium-bearing portion is arranged beside each of the plurality of working electrodes.

10. The implantable electrode as set forth in claim 1, wherein at least one liberation rate is predetermined for each of said at least one magnesium-bearing portion, such that each of said at least one magnesium-bearing portion is configured to be adapted individually to a respective liberation rate.

11. The implantable electrode as set forth in claim 1, wherein the at least one magnesium-bearing portion comprises a plurality of magnesium-bearing portions, such that at least a first magnesium-bearing portion of said plurality of magnesium bearing portions is carried on said proximal connecting region and at least a second magnesium-bearing portion of said plurality of magnesium bearing portions entirely covers said distal region.

12. The implantable electrode as set forth in claim 11, wherein said distal region comprises a holding structure or an anchor element, such that said at least second magnesium-bearing portion is arranged on or adjacent to said holding structure or said anchor element.

13. The implantable electrode as set forth in claim 1, wherein said at least one magnesium-bearing portion comprises a plurality of magnesium-bearing portions, such that each of said plurality of magnesium-bearing portions are configured to be integrated as independent metallic structures into said implantable electrode.

14. The implantable electrode as set forth in claim 13, wherein each of said plurality of magnesium-bearing portions configured to be integrated as independent metallic structures into said implantable electrode are in the form of ring structures.

15. The implantable electrode as set forth in claim 13, wherein each of said plurality of magnesium-bearing portions configured to be integrated as independent metallic structures into said implantable electrode are in the form of sleeves.

16. The implantable electrode as set forth in claim 1, wherein
said at least one electrical conductor comprises a plurality of recesses, and
said at least one magnesium-bearing portion comprises a plurality of magnesium-bearing portions;
such that each of said plurality of magnesium-bearing portions are configured to be integrated as independent metallic structures into said implantable electrode within a corresponding recesses of said plurality of recesses.

17. An implantable electrode which comprises
at least one electrical conductor having
a proximal connecting region for a pulse generator and a distal region; and
at least one working electrode configured to be connected to the pulse generator by way of the at least one electrical conductor,
wherein the at least one working electrode comprises an electrically active surface, and
wherein said at least one working electrode comprises a plurality working electrodes, such that a first working electrode and a second working electrode of said plurality of working electrodes are in the form of ring electrodes, and a third working electrode of said plurality of working electrodes is arranged at said distal region;
wherein the implantable electrode includes
at least one portion which contains
elementary magnesium in a form of metal particles,
wherein the metal particles are of a diameter between 0.1 μm and 500 μm;
wherein the elementary magnesium is configured such that a first period of time of decomposition starts immediately after implantation and is maintained until at least region-wise the implantable electrode is covered with connective tissue, such that the at least region-wise comprise at least regions of the elementary magnesium-containing portion that are covered to more than 50% of area with said connective tissue;
wherein the first period of time is between 1 and 90 days; and
wherein the elementary magnesium-containing portion is immediately adjacent to the at least one working electrode; and,
a plurality of magnesium-bearing portions;
wherein at least one magnesium-bearing portion of said plurality of magnesium-bearing portions covers the electrically active surface of the at least one working electrode,
wherein at least a first magnesium-bearing portion of said plurality of magnesium bearing portions is carried on said proximal connecting region, at least a second magnesium-bearing portion of said plurality of magnesium bearing portions entirely covers said distal region and directly adjoins said third working electrode, and at least a third magnesium-bearing portion of said plurality of magnesium bearing portions borders said first working ring electrode and said second working ring electrode;
wherein the at least one magnesium-bearing portion comprises a thickness between 10-100 µm and is configured such that a second period of time of decomposition is maintained, and such that the at least one magnesium-bearing portion comprises more than 90% by weight decomposed; and
wherein said second period of time is between 1 hour and 120 hours.

18. An implantable electrode which comprises
at least one electrical conductor having
a plurality of recesses;
a proximal connecting region for a pulse generator and a distal region; and
at least one working electrode configured to be connected to the pulse generator by way of the at least one electrical conductor,
wherein the at least one working electrode comprises an electrically active surface, and
wherein said at least one working electrode comprises a plurality working electrodes, such that a first working electrode and a second working electrode of said plurality of working electrodes are in the form of ring electrodes, and a third working electrode of said plurality of working electrodes is arranged at said distal region;
wherein the implantable electrode includes
at least one portion which contains
elementary magnesium in a form of metal particles,
wherein the metal particles are of a diameter between 0.1 µm and 500 µm;
wherein the elementary magnesium is configured such that a first period of time of decomposition starts immediately after implantation and is maintained until at least region-wise the implantable electrode is covered with connective tissue, such that the at least region-wise comprise at least regions of the elementary magnesium-containing portion that are covered to more than 50% of area with said connective tissue;
wherein the first period of time is between 1 and 90 days; and
wherein the elementary magnesium-containing portion is immediately adjacent to the at least one working electrode; and,
a plurality of magnesium-bearing portions;
wherein at least one magnesium-bearing portion of said plurality of magnesium-bearing portions covers the electrically active surface of the at least one working electrode,
wherein at least a first magnesium-bearing portion of said plurality of magnesium bearing portions is carried on said proximal connecting region, at least a second magnesium-bearing portion of said plurality of magnesium bearing portions entirely covers said distal region and directly adjoins said third working electrode, and at least a third magnesium-bearing portion of said plurality of magnesium bearing portions borders said first working ring electrode and said second working ring electrode;
wherein each of said plurality of magnesium-bearing portions are configured to be integrated as independent metallic structures into said implantable electrode within a corresponding recesses of said plurality of recesses;
wherein the at least one magnesium-bearing portion comprises a thickness between 10-100 µm and is configured such that a second period of time of decomposition is maintained, and such that the at least one magnesium-bearing portion comprises more than 90% by weight decomposed; and
wherein said second period of time is between 1 hour and 120 hours.

* * * * *